(12) United States Patent
Ahmed et al.

(10) Patent No.: US 9,079,770 B2
(45) Date of Patent: Jul. 14, 2015

(54) COMBINED REFORMING PROCESS FOR METHANOL PRODUCTION

(75) Inventors: Ijaz Ahmed, Riyadh (SA); Mubarak Bashir, Riyadh (SA); Abdullah Al-Nutaifi, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 361 days.

(21) Appl. No.: 13/390,474

(22) PCT Filed: Aug. 10, 2010

(86) PCT No.: PCT/EP2010/004972
§ 371 (c)(1),
(2), (4) Date: Feb. 14, 2012

(87) PCT Pub. No.: WO2011/018233
PCT Pub. Date: Feb. 17, 2011

(65) Prior Publication Data
US 2012/0149788 A1   Jun. 14, 2012

(30) Foreign Application Priority Data
Aug. 14, 2009  (EP) .................................. 09075363

(51) Int. Cl.
*C07C 29/151* (2006.01)
*C01B 3/38* (2006.01)

(52) U.S. Cl.
CPC .............. *C01B 3/382* (2013.01); *C07C 29/1518* (2013.01); *C01B 2203/0233* (2013.01);
(Continued)

(58) Field of Classification Search
CPC .............. C01B 3/382; C01B 2203/141; C01B 2203/061; C01B 2203/143; C01B 2203/0255; C01B 2203/0233; C07C 29/1518; C07C 31/04

USPC ........................................... 252/373; 518/703
See application file for complete search history.

(56) References Cited

U.S. PATENT DOCUMENTS

| | | | |
|---|---|---|---|
| 4,999,133 A | 3/1991 | Banquy | |
| 5,496,859 A | 3/1996 | Fong et al. | |

(Continued)

FOREIGN PATENT DOCUMENTS

| | | |
|---|---|---|
| CA | 2073526 A | 1/1993 |
| CN | 1033267 C | 11/1996 |

(Continued)

OTHER PUBLICATIONS

Extended European Search Report; European Application No. 09075363.3; Date of Mailing: Jan. 15, 2010; 7 Pages.
(Continued)

*Primary Examiner* — Jafar Parsa
*Assistant Examiner* — Amy C Bonaparte
(74) *Attorney, Agent, or Firm* — Cantor Colburn LLP

(57) ABSTRACT

The invention relates to a combined reforming process for making synthesis gas from a desulphurized gaseous hydrocarbon feedstock, wherein the feedstock is split into a first and a second feedstock stream, the first feedstock stream is mixed with steam and fed to a gas heated reformer (GHR) and a steam methane reformer (SMR) operated in series, and the second feedstock stream is mixed with reformed gas coming from the SMR and fed with oxygen to a non-catalytic partial oxidation reformer (POX). The process of the invention enables to produce syngas with adjustable composition and at very high capacity in a single line. The process specifically allows designing a methane-to-methanol production plant with a capacity exceeding 10000 mtpd using technically and economically feasible reforming equipment, and showing high feedstock and energy efficiency. The invention further relates to an integrated process for making methanol from a hydrocarbon feedstock comprising said combined reforming process.

12 Claims, 1 Drawing Sheet

(52) U.S. Cl.
CPC ... *C01B2203/0255* (2013.01); *C01B 2203/061* (2013.01); *C01B 2203/141* (2013.01); *C01B 2203/143* (2013.01)

(56) References Cited

U.S. PATENT DOCUMENTS

| | | | |
|---|---|---|---|
| 5,512,599 | A | 4/1996 | Hiramatsu et al. |
| 6,100,303 | A | 8/2000 | Hirotani et al. |
| 6,444,712 | B1 | 9/2002 | Janda |
| 8,388,864 | B2 | 3/2013 | Bormann et al. |
| 2004/0063797 | A1 | 4/2004 | Aasberg-Petersen et al. |
| 2007/0004809 | A1* | 1/2007 | Lattner et al. ............... 518/700 |

FOREIGN PATENT DOCUMENTS

| | | |
|---|---|---|
| CN | 101448731 A | 6/2009 |
| EP | 0522744 A2 | 1/1993 |
| EP | 0959120 A1 | 11/1999 |
| EP | 1241130 A1 | 9/2002 |
| EP | 1403216 A1 | 3/2004 |
| GB | 2160516 A | 12/1985 |
| GB | 0440258 A2 | 8/1991 |
| GB | 2407819 A | 6/2006 |
| WO | 9315999 A1 | 8/1993 |
| WO | 2005070855 A1 | 8/2005 |
| WO | 2006117499 A1 | 11/2006 |
| WO | 2008122399 A1 | 10/2008 |

OTHER PUBLICATIONS

"Methanol"; Ullmann's Encyclopedia of Industrial Chemistry; Published by Wiley-VCH Verlag; DOI: 10.1002/14356007.a16_465; Available Online: Jun. 15, 2000.

P.F. van den Oosterkamp; "Synthesis Gas Generation: Industrial"; Encyclopedia of Catalysis; Published by John Wiley & Sons; DOI: 10.1002/0471227617.eoc196; Available Online: Dec. 13, 2002.

International Search Report; International Application No. PCT/EP2010/004972; International Filing Date: Aug. 10, 2010; Date of Mailing: Oct. 8, 2010; 7 Pages.

Written Opinion of the International Searching Authority; International Application No. PCT/EP2010/004972; International Filing Date: Aug. 10, 2010; Date of Mailing: Oct. 8, 2010; 5 Pages.

* cited by examiner

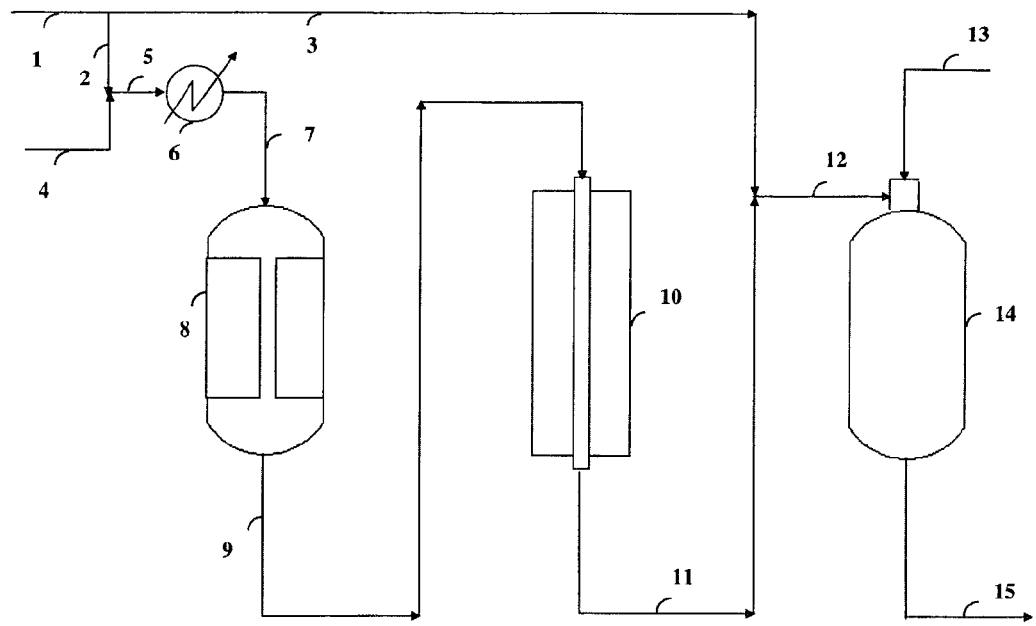

COMBINED REFORMING PROCESS FOR METHANOL PRODUCTION

CROSS REFERENCE TO RELATED APPLICATIONS

This application is a 371 of International Application No. PCT/EP2010/004972, filed Aug. 10, 2010, which claims priority to European Application No. 09075363.3, filed Aug. 14, 2009, both of which are hereby incorporated by reference in its entirety.

TECHNICAL FIELD

The invention relates to a combined reforming process for making a synthesis gas mixture, especially a synthesis gas mixture suitable for methanol production, from a desulphurised hydrocarbon feedstock, wherein a combination of different reforming reactors is used. The invention further relates to a process for making methanol from a hydrocarbon feedstock comprising this combined reforming process.

BACKGROUND

Such a combined reforming process is known from patent publication U.S. Pat. No. 6,100,303. In this document a process for making synthesis gas for subsequent use in methanol production is described, wherein a desulphurised feedstock gas consisting of a hydrocarbon gas having an H/C atomic ratio of 3-4, for example natural gas composed mainly of methane, is reformed using a combination of 3 different reforming reactors. The feedstock is first mixed with steam and then fed to a combustion-type (also called fired) steam methane reforming reactor (steam methane reformer, hereinafter abbreviated as SMR) and a heat-exchange type steam reforming reactor that is heated with hot gasses produced elsewhere in the process (also called gas heated reformer, hereinafter abbreviated as GHR), which two reactors are operated in parallel arrangement. The effluent gasses from SMR and GHR are mixed and fed to a secondary reforming unit together with oxygen, wherein the gasses undergo a catalytic partial oxidation reaction under essentially adiabatic conditions in addition to further reaction with steam. This reforming reactor is also referred to as auto-thermal reformer (abbreviated as ATR), as the excess heat generated by exothermic reaction is used to supply heat for the endothermic steam reforming reaction. The SMR unit is heated by burning part of the hydrocarbon feedstock gas and a purge of synthesis gas. The feed ratio of feedstock gas to the SMR and GHR units can vary from 1-3 to 3-1.

In the past decades, numerous processes have been developed to produce synthesis gas (also referred to in short as syngas) as one of the most important feedstocks in chemical industry. Syngas is a gaseous mixture containing hydrogen ($H_2$) and carbon monoxide (CO), which may further contain other gas components like carbon dioxide ($CO_2$), water ($H_2O$), methane ($CH_4$), and nitrogen ($N_2$). Natural gas and (light) hydrocarbons are the predominant starting material for making synthesis gas. Syngas is successfully used as synthetic fuel and also in a number of chemical processes, such as synthesis of methanol or ammonia, Fischer-Tropsch type and other olefin syntheses, hydroformulation or carbonylation reactions (oxo processes), reduction of iron oxides in steel production, etc. The composition of synthesis gas, and thus its suitability for subsequent use for e.g. methanol production, is characterized mainly by its hydrogen and carbon monoxide content; generally presented by the so-called stoichiometric number (SN), which is defined as $$SN=([H_2]-[CO_2])/([CO]+[CO_2])$$

wherein the concentrations of components are expressed in vol % or mol %.

The value of SN is highly dependent on the reforming process technology used to make syngas. An overview of different technologies and their advantages and limitations is for example given by P. F. van den Oosterkamp in chapter "Synthesis Gas Generation: Industrial" of the "Encyclopedia of Catalysis" (John Wiley & Sons; posted on-line 2002/12/13, available via DOI: 10.1002/0471227617.eoc196).

The conventional technology for producing syngas from a methane feedstock is the reaction with water (steam) at high temperatures, generally called hydrocarbon steam reforming.

If a feedstock is used in a reforming process that is rich in higher hydrocarbons, like naphtha, the feedstock first needs to be treated in a so-called pre-reforming step, in order to convert the heavy hydrocarbons in the feed into methane, hydrogen and carbon oxides. Such higher hydrocarbons are more reactive than methane in steam reforming, and would—if present in the feed—lead to carbon formation and thus to deactivation of the catalyst employed in steam reforming. In such a pre-reformer several reactions take place simultaneously; the most important being hydrocarbon steam reforming (1), water gas shift (2), and methanation (3) reactions, which can be represented, respectively, as:

  (1)

  (2)

$$CO_2+4H_2 \leftrightarrows CH_4+2H_2O \quad (3)$$

Such a pre-reformer is typically operated adiabatically at temperatures between 320 and 550° C., and is generally referred to as an adiabatic pre-reformer (hereinafter abbreviated as APR).

In a steam methane reformer (SMR) methane-rich gas is converted into a mixture containing carbon monoxide, carbon dioxide, hydrogen and unreacted methane and water in the so-called steam reforming (4) and carbon dioxide reforming (5) reactions, represented as:

  (4)

  (5)

These reforming reactions are strongly endothermic, while the accompanying water gas shift reaction is moderately exothermic. Such process thus calls for a reactor wherein heat management is extremely important. For the steam reforming process, several types of reactors are possible, such as the conventional widely used top-fired or side-fired reformers. In practice, a SMR unit may contain from 40 up to 1000 tubes, each typically 6-12 m long, 70-160 mm in diameter, and 10-20 mm in wall thickness. These tubes are vertically placed in a rectangular furnace or firebox, the so-called radiant section. The reactor tubes contain nickel-based catalyst, usually in the form of small cylinders or rings. The reactor tubes are fired by burners, which may be located at the bottom, at the side, or at the top of the furnace. Combustion of the fuel takes place in the radiant section of the furnace. After the flue gas has supplied its heat to all the reactor tubes, it passes into the convection section where it is further cooled by heating other streams such as process feed, combustion air, and boiler feed water as well as producing steam. The product gas, typically leaving the reformer at a temperature of 850-950° C., is cooled in a process gas waste heat boiler to produce process steam for the reformer. The syngas made with conventional steam reforming typically has a SN of between 2.6 and 2.9. For methanol production a composition having SN coming close to the theoretical value of 2 is preferred. The SN value of the syngas composition can be lowered by for example adding carbon dioxide; or by combined reforming (see below).

Steam reforming can also be performed in reactors wherein the necessary heat is supplied by heat exchange rather than by direct firing, for example by convective heat transfer from hot flue gasses and/or from hot syngas produced at another stage of a process. Several reactor concepts have been developed for this purpose, the name gas heated reformer (GHR) generally being used for a reactor that makes use of the heat present in syngas that is being produced in an auto-thermal reforming unit (ATR) or in a partial oxidation reformer; see below.

In an ATR catalytic conversion of a methane feedstock with oxygen (as pure oxygen, air, or enriched air) takes place in combination with the conversion with steam; an ATR is basically a combination of SMR and partial oxidation technology. In addition to the reactions mentioned above, also following strongly exothermic partial oxidation reactions (6) take place:

$$CH_4 + \tfrac{3}{2}O_2 \leftrightarrows CO + 2H_2O \qquad (6)$$

Desulphurised feedstock mixed with steam is introduced into the ATR reactor, as is oxygen in an appropriate amount. The upper part of the reactor basically consists of a burner mounted in the reactor shell. The exothermic reaction with oxygen delivers the endothermic heat of reaction of the steam reforming reaction, such that the overall reaction is autothermal, and takes place in the upper part; whereas the catalyzed reforming reaction takes place in a fixed bed in the lower part. Operating temperatures are relatively high, typically up to 1000° C., enabling very low amounts of unconverted methane in the product gas. The syngas produced in an ATR has a relatively low concentration of hydrogen; for subsequent methanol production mixing with hydrogen from another source will be needed.

Several process schemes that combine a steam reformer and an ATR unit (or a partial oxidation reactor) in different lay-outs have been proposed. Advantages of such combined reforming processes include controlling the SN of the syngas made at a targeted value.

As already indicated above, a combination of ATR and GHR technologies makes more efficiently use of energy; a further advantage being that adjustment of the SN of the syngas, e.g. close to the value of 2 as desired for methanol production, is possible.

WO 93/15999 A1 describes a process of making syngas by dividing a feed gas stream over a steam reformer and a partial oxidation reactor, and feeding the combined effluent streams to a second steam reformer.

In U.S. Pat. No. 4,999,133 a process for making syngas suitable for methanol production is disclosed, wherein a part of the feed is passed over a steam reformer, and resulting effluent and the other part of feed are fed to an ATR unit.

U.S. Pat. No. 5,512,599 relates to a process for making methanol from syngas on a large scale and with high energy efficiency, comprising a first step of steam reforming a hydrocarbon feed in a GHR reactor, followed by a partial oxidation and a second steam reforming step in an ATR unit, wherein effluent gas from ATR is used as a heat source for the GHR.

U.S. Pat. No. 6,444,712 B1 discloses a process for making methanol from syngas, wherein a methane feed is split and supplied to an ATR and a SMR operated in parallel, and effluent streams are fed to subsequent methanol synthesis. Unreacted syngas is recovered from methanol effluent and used for making hydrocarbons.

U.S. Pat. No. 5,496,859 discloses a process for making methanol from syngas, wherein a desulphurised methane-rich feed is supplied to an ATR and a SMR operated in parallel, and effluent streams are combined and fed to a second ATR to result in a syngas of proper composition and pressure for subsequent methanol synthesis.

EP 0522744 A2 describes a process for making a.o. methanol from syngas, wherein a desulphurised hydrocarbon feedstock is divided into 2 streams, of which a first stream is fed to a SMR unit, and a second stream is fed to an APR and a partial oxidation reactor operated in series, followed by cooling and mixing both reformed streams.

US 2004/0063797 A1 describes a process for making syngas especially suited for subsequent use in Fischer-Tropsch synthesis, wherein a desulphurised hydrocarbon feedstock is reformed in an APR, one or more steam reformers and an ATR, which are all operated in series.

EP 1403216 A1 describes a process for making syngas especially suited for subsequent use in Fischer-Tropsch synthesis, wherein a desulphurised hydrocarbon feedstock is reformed in one or more steam reformers and an ATR, which is operated in parallel with the other reformers.

GB 2407819 A discloses a process of making syngas from a hydrocarbon, e.g. natural gas, which process employs a combination of 3 reforming units, wherein the feed first passes an APR and then is split and fed to SMR and ATR units operated in parallel; to enable high syngas production capacity.

EP 1241130 A1 discloses a process of making syngas from light natural gas, by first treating the feed in an APR unit at 500-750° C. with a special catalyst, followed by conventional steam reforming; in order to reduce the heat supply required in steam reforming.

In EP 0440258 A2 a steam reforming process with improved reutilisation of heat is proposed, wherein a desulphurised hydrocarbon feed is first reacted in a first GHR, and the gas stream is then divided into 2 parallel streams, of which the first stream is fed to a SMR and the second stream to a further GHR, after which the effluent streams are combined and fed to an ATR unit.

EP 0959120 A1 discloses combined steam reforming processes aiming to optimise the energy efficiency by using heat from combustion gasses, including a scheme wherein GHR, SMR and ATR units are operated in series, and a scheme wherein the feed is fed to GHR and SMR units operated in parallel followed by reacting the combined effluent streams in an ATR.

WO 2005/070855 A1 describes an integrated process for making methanol and acetic acid from natural gas, wherein syngas is made by reacting part of the feed gas in an APR and SMR operated in series, and reforming the effluent combined with the remainder of the natural gas in an ATR.

In WO 2008/122399 A1 a combined reforming process for making a syngas mixture from a desulphurised methane-rich gaseous feedstock is disclosed, wherein the gaseous feedstock is mixed with steam and passed through an APR, and wherein the pre-reformed gas is then divided into three streams that are fed to a SMR, a GHR and to an ATR, which reforming reactors are operated in parallel. This process is stated to allow designing a methane-to-methanol production plant with a capacity of at least 10000 mtpd using available reforming equipment.

Methanol is one the most important chemical raw materials; in 2000 about 85% of the methanol produced would be used as a starting material or solvent for synthesis, whereas its use in the fuel and energy sector has been increasing rapidly. Since the 1960's, methanol synthesis from sulphur-free syngas with Cu-based catalysts has become the major route, as it can be operated at fairly mild reaction conditions. An overview of such methanol processes can be found in for example in the chapter "Methanol" in "Ullmann's Encyclopedia of Industrial Chemistry" (Wiley-VCH Verlag; posted on-line 2000 Jun. 15, available via DOI: 10.1002/14356007.a16_ 465).

Regarding the increasing demand for fuel and energy, there is a need in industry for ever larger and more efficient methanol production plants. Presently operated integrated production processes for making methanol from hydrocarbon feedstock typically have a maximum single line capacity on the order of 5000-7000 mtpd (metric ton per day). Practical limitations are encountered especially in syngas production, i.e. in the maximum size of available reforming reactors and of air separation units producing the required oxygen.

For example, limitations in the maximum size of a SMR unit lay in the number of tubes, in even gas distribution, and in heat transfer. About 1000 tubes is considered to be the maximum for a single unit operation, otherwise it will not be possible to control uniform distribution of gasses and thus of heat to all tubes. Reliability of all units is paramount, as minimizing down-time is a prerequisite for economical operation. Further capacity limitation results from a certain maximum amount of energy that can be transferred to the tubes. It is thus estimated that a technically and economically feasible SMR reactor of maximum capacity is characterized by a maximum reforming heat load of about 1150 GJ/h.

Production capacity of a GHR unit is mainly limited by a practical maximum in energy input by heat exchange with hot gasses; which is estimated to be about 420 GJ/h.

Presently available ATR or other partial oxidation units do not have the above limitations of steam reformers, but the maximum production capacity in this case is in practice limited by the volume of oxygen that is available. In most cases, oxygen is to be supplied from an air separation unit (abbreviated as ASU). The maximum size of a single state-of-the-art ASU is for technical and economical reasons considered to be about 4000 mtpd; which is equivalent to about 5200 kmol/h of oxygen. The equivalent maximum methanol production capacity based on such a single partial oxidation unit would be about 4500-6000 mtpd.

Although integrated production processes for making methanol from hydrocarbon in practice have a maximum single line capacity of about 6000 mtpd, schemes for larger scale plants have been proposed. Such schemes, however, typically employ operating units that exceed one of the above discussed maxima and practical limitations.

SUMMARY

There is thus a need in the industry for a combined reforming process that enables a single-line process for making methanol from a hydrocarbon feedstock with very large capacity, preferably of at least 10000 mtpd, and which reforming process uses reforming reactors and other equipment with capacities within current practical limitations.

BRIEF DESCRIPTION OF THE DRAWING

FIG. 1 is a process flow diagram of an embodiment of a reforming process.

DETAILED DESCRIPTION

This object is achieved according to the present invention as defined in the description and claims, more specifically with a combined reforming process for making a synthesis gas mixture from a desulphurised gaseous hydrocarbon feedstock, wherein the feedstock is divided into a first and a second feedstock stream, the first feedstock stream is mixed with steam and fed to a gas heated reformer (GHR) and a steam methane reformer (SMR) operated in series, and the second feedstock stream is mixed with reformed gas coming from the SMR and fed with oxygen to a non-catalytic partial oxidation reformer (POX).

With the process according to the invention it is possible to produce syngas with adjustable composition and at very high capacity in a single line. The process allows designing e.g. a methane-to-methanol production plant with a capacity of at least 10000 mtpd using technically and economically feasible reforming equipment. The process further shows high energy efficiency. A further advantage is that the process has low methane leakage, meaning that the final syngas has a low content of inerts, resulting in a high overall conversion of feedstock to methanol. Further, the high-capacity single-line syngas process reduces the investments required per ton of methanol production capacity.

It is true that WO 2008/122399 A1 also proposes a methane-to-methanol production plant with a capacity of at least 10000 mtpd using technically and economically feasible reforming equipment, but the scheme of the current invention is less complex. In addition, by applying GHR and SMR reactors in series more efficient use is made of SMR capacity. A further advantage is that a POX reactor is used rather than an ATR, which POX is operated without catalyst and at very high temperatures of up to 1400° C., thus allowing further capacity increase. The steam to carbon ratio can also be lower, steam/carbon is typically about 1 but may be as low as 0.2, enabling use of a wider range of feedstock, including light naphtha, without including an APR.

In the process of the present application the gaseous hydrocarbon feedstock can be any hydrocarbon mixture having H/C ratio of about 2 to 4 that is gaseous at reactor inlet operating conditions, i.e. at about 300° C. Suitable examples include hydrocarbons like methane, ethane, methane-rich mixtures, or light naphtha (mixture of mainly C5-C9 paraffin compounds)

A suitable example of a methane-rich feedstock is natural gas, as obtained from gas or oil fields. The primary component of natural gas is methane, which is generally present in amounts of from 80 to 97 mol %. Natural gas also contains other gaseous hydrocarbons such as ethane, typically from about 3 to 15 mol %, propane, butane and small amounts of higher hydrocarbons (generally less than 5 mol % in total), as well as sulphur-containing gases, like hydrogen sulphide, in varying amounts. Further minor (or even trace) amounts of nitrogen, helium, carbon dioxide, water, odorants, and metals like mercury can also be present. The exact composition of natural gas varies with its source.

Organo-sulphur compounds and hydrogen sulphide are common contaminants of hydrocarbons from natural sources, which should be removed prior to use of hydrocarbon gas as a feedstock in the present process, to avoid poisoning of reforming catalysts. Desulphurisation can be done with conventional techniques. In a suitable process, the gaseous feedstock is first compressed to 3-4 MPa with a centrifugal or reciprocating compressor. A hydrogen-rich stream (for example a purge stream from a methanol synthesis loop) is mixed with the gas, usually after compression, and hydrogen concentration in the gas is maintained at a level of 2-5 vol %. The stream is preheated to 350-380° C. and passed over an adiabatic catalytic reactor containing a hydrodesulphurisation catalyst, e.g. Co—Mo— or Ni—Mo-based. The organosulphur compounds in the feedstock are converted to $H_2S$, which is subsequently removed by passing over a suitable absorbent, like ZnO, in a down stream vessel. Preferably, the sulphur content of the desulphurised gaseous feed is at a level of below 1 ppm.

Preferably, the desulphurised hydrocarbon feedstock that is used in the process according to the invention is a methane-rich feedstock that contains as least 75 mol % of methane (based on total hydrocarbon content of the feedstock), more preferably at least 80, 85, 90, 92, 94 even at least 96 mol % of methane.

In the process according to the invention the desulphurised hydrocarbon feedstock is divided in to two streams. The first feedstock stream is mixed with steam and then fed to a gas heated reformer (GHR) and a steam methane reformer (SMR) that operated in series. This first feedstock stream forms preferably from about 40 to 55 vol % of the total feedstock, more preferably 45-50 vol %, for optimum use of maximum amount of oxygen available from an ASU and allowable heat loads of SMR and GHR. The relative stream volumes are chosen to result in optimised process efficiency and composition of the syngas, depending on its use. For example, SN of the final syngas stream formed is preferably between 2.0 and 2.2 for subsequent use in methanol synthesis.

Mixing with steam is typically done at a pressure of about 3-5 MPa and a temperature of about 350-400° C. In this stream, a steam to carbon ratio of from about 2.0 to 3.5, preferably 2.2-3.0 or 2.3-2.7, is maintained, and the mixed feed stream is preferably preheated to about 500-550° C., for example with a heat exchanger. For this purpose preferably a heat exchanger coil that is installed in the convection duct of the steam methane reformer is used.

The preheated mixed feed stream is then passed through a conventional gas heated reformer, which typically contains a conventional Ni-based reforming catalyst. In the GHR also higher hydrocarbons—if present—are converted, and part of the methane is steam reformed to CO, $CO_2$ and $H_2$. The extent of reforming depends on various factors, such as feed preheat temperature, operating pressure, feed gas composition and steam to carbon ratio. The design of the GHR is not critical, and available designs can be applied to make a unit of suitable size for the present process. The heat for this reactor is provided by hot effluent gas from the POX reactor. Typical operating conditions include a pressure of about 2-4 MPa and temperature of 500-870° C., preferably 600-700° C.

The partly reformed gas stream coming from the GHR generally has a temperature of about 600-700° C., more preferably of about 625-675° C., and is subsequently fed to the SMR unit at a pressure of about 2-4 MPa. The design of the SMR is not critical, and available designs can be applied to make a unit of suitable size for the present process Typical operating conditions for SMR include a pressure of about 1-4 MPa, preferably 3-4 MPa, and a temperature of 450-900° C., preferably 700-900 or 800-880° C. The relatively high starting temperature of inlet gas for SMR as compared to other processes applying SMR units significantly reduces heat load requirements and promotes conversion to syngas in this reactor, and thus boosts SMR output capacity.

Reformed gas coming as effluent from the SMR may still contain some methane in addition to CO, $CO_2$, $H_2$, $N_2$ and $H_2O$, which will further react in the POX unit; for example the effluent contains about 6-8 vol % of $CH_4$ (on dry basis).

In the process according to the invention the second part of the divided or split desulphurised hydrocarbon feedstock, which second feedstock stream constitutes from 60 to 45, preferably 55-50 vol % of the total feedstock, is mixed with reformed gas coming from the SMR as effluent stream. Mixing can be done with conventional equipment, at for example 3-4 MPa and 700-750° C. Preferably, all reformed effluent from SMR is mixed with the second feedstock stream.

The resulting mixture is subsequently fed to a non-catalytic partial oxidation reactor (POX), together with oxygen. It can thus also be stated that the GHR and SMR reactors are operated both in parallel and in series with the POX reactor.

The ratio of the SMR reformed gas and second feedstock stream mixture to oxygen depends on composition of the mixture and desired composition (SN) of the resulting syngas, and the skilled can make a proper selection. A boundary condition is the maximum supply rate of oxygen of about 5200 kmol/h, based on estimated maximum size of a single ASU in current practices, which thus limits the capacity of the POX unit.

Although in literature partial oxidation reactions are performed with and without a catalyst, within the context of the present application a POX reforming unit is defined as a reactor wherein non-catalytic partial oxidation reactions take place. A POX reformer is thus different from an ATR unit; as it can be operated with less steam, typically steam/carbon ratio is below 1, and at higher temperatures of up to 1500° C.

The design of the POX is not critical, and available designs can be applied to make a unit suitable for the present process. Typical operating conditions for POX include a pressure of about 2-5 MPa, preferably 3-4 MPa, and a temperature of about 900-1400° C., preferably 1000-1300° C.; resulting in effluent with temperature of about 1000-1300° C.

The syngas stream coming from the POX unit is then cooled, at least in part by heat exchanging with the GHR unit, and compressed in case of subsequent methanol synthesis steps.

Energy consumption of the POX unit in the process according to the invention is estimated to be about 5 to 6% less than that of an ATR unit. Steam consumption, however, is significantly lower, because of the lower steam/carbon ratio: steam consumption is estimated to be only about 50% of that for an ATR. Considering also GHR and SMR units have lower heat load requirements, it is clear that the process according to the invention shows significantly lower overall energy consumption than prior art processes.

In the process according to the invention more than one unit of each of the 3 different reforming reactors may be applied, but the process preferably comprises one unit of each type of reformer; that is one GHR, one SMR and one POX unit; in view of minimising plant complexity and investment costs.

The above described process is further illustrated by the scheme in FIG. 1, providing a simplified process flow diagram of an embodiment of the process according to the invention. In this FIGURE reference numbers used are further elucidated in the text below.

In FIG. 1 a desulphurised methane-rich gas stream 1 of pressure of about 4 MPa and a temperature of about 375° C. is split into streams 2 and 3, at a volume ratio of 45/55.

Stream 2 is then mixed with a steam stream 4 at a pressure of about 4 MPa and a temperature of about 400° C., and at a steam to carbon ratio of about 2.5. This mixed stream 5 is then preheated to about 550° C. in heat exchange coil 6, which coil can be heated by hot flue gases in convection duct of the SMR 10. Preheated mixed stream 7 is then partially reformed in GHR 8, which contains conventional nickel-based catalyst and is heated by hot effluent stream from POX 14. The reformed stream 9 leaves the GHR at about 650° C., and is then fed to SMR 10. Stream 11 coming from the SMR at a temperature of about 870° C. is then mixed with feedstock stream 3, and fed to POX 14, as is oxygen stream 13. POX 14 is operated at pressure 3 MPa and temperatures of about 1000° C., resulting in syngas outlet stream 15 of about 1000° C. After heat recovery and cooling this stream is sent to further processing units, dependent on desired final product(s).

The syngas mixture that is obtained by the process according to the invention can be used for various purposes, preferably as a starting material in a process of making a chemical compound, optionally in an integrated process. Suitable examples thereof include synthesis of methanol and/or ammonia, Fischer-Tropsch type and other olefin synthesis processes, and hydroformulation or carbonylation reactions (oxo processes).

Preferably, the syngas made with the process according to the invention is used for making methanol, more preferably the syngas is used directly to make methanol in an integrated process.

Preferably, in the process according to the invention the gas distribution rates, and operating conditions of the reformers are adjusted, within above indicated ranges, such that the composition of the syngas product stream is suitable for subsequent use in methanol synthesis; i.e. preferably the syngas mixture has a SN of 2.0-2.2, more preferably SN is 2.0-2.1.

The invention further relates to an integrated process for making methanol from a hydrocarbon, preferably a methane-rich, gaseous feedstock comprising the combined reforming process according to the invention, with preferred process schemes and conditions as described above. In such a process following process steps can be distinguished: (a) syngas production, (b) methanol synthesis, and (c) methanol distillation. In the methanol process according to the invention known processes can be applied for steps (b) and (c); as for example described in the above referenced chapter in Ullmann's Encyclopedia of Industrial Chemistry.

In the integrated methanol process according to the invention, there can be various couplings between the steps (a), (b) and (c) to optimize consumption of feedstock and energy. Examples hereof include use of hot boiler water from syngas steps in methanol synthesis, and recirculation of unreacted syngas components from methanol synthesis back to methanol synthesis loop or using it as fuel for the SMR.

The present invention is now further elucidated with the following experiments, which includes a process simulation of the scheme depicted in FIG. 1.

EXAMPLES

In the following production of methanol from a methane-rich gas with a process according to the flow scheme is simulated using a standard simulation package, such as Pro-II, taking into account boundary conditions for the reforming reactors as described in the above:

SMR unit: maximum heat load about 1150 GJ/h;
GHR unit: maximum energy input 420 GJ/h;
POX unit: limited by maximum ASU capacity of about 5200 kmol/h of oxygen.

Table 2 shows the simulation results for syngas production for a methanol production capacity of 10000 mtpd based on the flow rates, compositional data, temperatures and pressures as provided by U.S. Pat. No. 6,100,303 in Example 3 and Table 3; now re-named as Comparative experiment A. The composition of the natural gas used as feed in the experiment is given in Table 1.

The resulting data as listed in Table 2 are in good agreement with figures reported in U.S. Pat. No. 6,100,303, e.g. in Table 6 therein. It is noted that indicated heat load is the heat required for carrying out the reforming reaction, not the fuel requirement. Carbon efficiency is defined as the total molar flow rates of CO and $CO_2$ converted to methanol relative to the total molar flow rates of CO and $CO_2$ in the syngas. From these data it can be concluded that in the experiment according to the process as disclosed in U.S. Pat. No. 6,100,303 energy requirement exceeds practical limitations for the GHR equipment as discussed hereinabove.

TABLE 1

| | Composition of natural gas feedstock (vol %) | |
|---|---|---|
| Component | Comp. exp. A | Comp. exp. B Example 1 |
| $CH_4$ | 95.60 | 89.54 |
| $C_2H_6$ | 3.39 | 3.91 |
| $C_3H_8$ | 0.09 | 0.48 |
| $C_4H_{10}$ | 0.18 | 0.24 |
| $C_5H_{12}$ | | 0.08 |
| CO | | 0.00 |
| $CO_2$ | 0.47 | 0.30 |
| $N_2$ | 0.26 | 5.45 |
| $H_2O$ | 0.01 | |
| total | 100 | 100 |

Table 2 also shows simulation results for syngas production for methanol production as given in WO2008/122399A1 in Example 2 and Table 3; now re-named as Comparative experiment B. The composition of the natural gas used as feed in the experiments is given in Table 1. This flow scheme utilises 4 different reformers that are operated close to their maximum feasible capacities, and also enables methanol production rate of over 10000 mtpd.

In Table 2 also results are given as Example 1 for simulations based on the process flow scheme according to the current invention. In this simulation a final syngas stream with SN 2.19 is made from a methane-rich natural gas of composition as given in Table 1, to enable subsequent methanol production with a capacity of at least 10000 mtpd, utilising available GHR, SMR, and POX (and ASU) single line equipment.

It can be concluded that methanol production rates significantly exceeding 10000 mtpd are possible with the flow scheme according to the process of the invention, because both the SMR and GHR units are operated well below their maximum feasible capacities (see Table 1). Alternatively, smaller reactor units may be employed in a single line plant of about 10000 mtpd capacity, thus further lowering investment costs.

TABLE 2

|  | unit | CE A Based on U.S. Pat. No. 6,100,303 | CE B Based on WO2008/122399 | Example 1 |
|---|---|---|---|---|
|  |  | Feed: | Feed: | Feed: |
| Total gaseous feed rate | kmol/h | 12974 | 15074 | 14733 |
| Gaseous feed pressure | MPa | 2.7 | 4.1 | 4.0 |
|  |  |  | APR unit: |  |
| Mixed gas feed rate | kmol/h |  | 53303 |  |
| Steam to Carbon ratio |  |  | 2.5 |  |
| Gas inlet temperature | °C. |  | 500 |  |
| Gas exit temperature | °C. |  | 446 |  |
|  |  | GHR unit: | GHR unit: | GHR unit: |
| Mixed gas feed rate | kmol/h | 32339 | 13804 | 23434 |
| Steam to Carbon ratio |  | 2.5 | 2.5 | 2.5 |
| Gas inlet temperature | °C. | 360 | 650 | 550 |
| Gas exit temperature | °C. | 726 | 750 | 650 |
| Methane leakage | vol % | 20.8 | 21.3 | 36.6 |
| Heat load | GJ/h | 1392 | 364 | 102 |
|  |  | SMR unit: | SMR unit: | SMR unit: |
| Mixed gas feed rate | kmol/h | 14259 | 15146 | 26917 |
| Steam to Carbon ratio |  | 2.5 | 2.5 | 2.7 |
| Gas inlet temperature | °C. | 560 | 650 | 650 |
| Gas exit temperature | °C. | 800 | 870 | 870 |
| Methane leakage | vol % | 10.6 | 8.7 | 7.6 |
| Heat load | GJ/h | 726 | 741 | 232 |
|  |  | ATR unit: | ATR unit: | POX unit: |
| Mixed gas feed rate | kmol/h | 60450 | 43065 | 41462 |
| Oxygen feed rate | kmol/h | 4583 | 5208 | 5208 |
| Steam to Carbon ratio |  | 3.5 | 2.7 | 1.02 |
| Gas inlet temperature | °C. | 749 | 685 | 729 |
| Gas exit temperature | °C. | 975 | 985 | 1000 |
| Methane leakage | vol % | 0.4 | 0.7 | 2.3 |
| Heat loss | GJ/h | 171 | 0 | 0 |
|  |  | Product: | Product: | Product: |
| Total syngas flow rate (dry) | kmol/h | 47750 | 50791 | 48064 |
| SN |  | 2.25 | 2.18 | 2.19 |
| Methane leakage (overall) | vol % | 0.4 | 2.9 | 2.3 |
| Carbon efficiency | % | 98 | 95 | 95 |
| Methanol production rate | mtpd | 10000 | 10000 | 10000 |

The invention claimed is:

1. A combined reforming process for making a synthesis gas mixture from a desulphurised gaseous hydrocarbon feedstock, wherein the feedstock is divided into a first and a second feedstock stream, the first feedstock stream is mixed with steam and fed to a gas heated reformer (GHR) and a steam methane reformer (SMR) operated in series, and the second feedstock stream is mixed with reformed gas coming from the SMR and fed with oxygen to a non-catalytic partial oxidation reformer (POX),
    wherein said synthesis gas mixture produces methanol and wherein the combined reforming process produces at least 10,000 metric tons of methanol per day.

2. The process according to claim 1, wherein the hydrocarbon feedstock is a methane-rich feedstock containing at least 80 mol % of methane.

3. The process according to claim 1, wherein the first feedstock stream forms 45-50 vol % of the feedstock and is mixed with steam at steam/carbon ratio of 2.3-2.7.

4. The process according to claim 1, wherein the first feedstock stream mixed with steam is preheated to 500-550° C. and then fed to the GHR.

5. The process according to claim 1, wherein partly reformed gas coming from the GHR has a temperature of 625-675° C., and is subsequently fed to the SMR.

6. The process according to claim 1, wherein all reformed gas from the SMR is mixed with the second feedstock stream.

7. The process according to claim 1, which comprises one GHR, one SMR and one POX unit.

8. The process according to claim 1, wherein the synthesis gas mixture obtained has a stoichiometric number of 2.0-2.2.

9. The process for making methanol from a hydrocarbon feedstock comprising the combined reforming process according to claim 1.

10. The process according to claim 1, wherein the non-catalytic partial oxidation reformer has an operating pressure of 3 to 4 MegaPascals.

11. The process according to claim 1, wherein the non-catalytic partial oxidation reformer operates with steam.

12. The process according to claim 11, wherein the ratio of steam to carbon is less than or equal to 1.2.

* * * * *